(12) United States Patent
Wen

(10) Patent No.: US 7,819,659 B2
(45) Date of Patent: Oct. 26, 2010

(54) SYSTEM FOR ORGANIZING DENTAL ALIGNERS

(75) Inventor: Huafeng Wen, Redwood City, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 11/205,496

(22) Filed: Aug. 16, 2005

(65) Prior Publication Data

US 2006/0240374 A1    Oct. 26, 2006

Related U.S. Application Data

(60) Provisional application No. 60/675,003, filed on Apr. 25, 2005, provisional application No. 60/676,546, filed on Apr. 29, 2005, provisional application No. 60/676,278, filed on Apr. 29, 2005, provisional application No. 60/676,100, filed on Apr. 29, 2005, provisional application No. 60/676,546, filed on Apr. 29, 2005.

(51) Int. Cl.
*A61C 3/00* (2006.01)
(52) U.S. Cl. .......................................... 433/6; 206/63.5
(58) Field of Classification Search ............... 433/24, 433/6; 206/63.5, 558
See application file for complete search history.

(56) References Cited

U.S. PATENT DOCUMENTS

| | | | |
|---|---|---|---|
| 1,813,583 A | 7/1931 | Rice | |
| 2,037,344 A | 4/1936 | Schwartz | |
| 2,138,254 A | 11/1938 | Mink | |
| 2,700,218 A | 1/1955 | Lindley | |
| 3,218,711 A | 11/1965 | Connan | |
| 3,436,829 A | 4/1969 | Jermyn | |
| 3,453,736 A | 7/1969 | Waltke | |
| 3,470,614 A | 10/1969 | Kelly | |
| 3,576,075 A | 4/1971 | Scott | |
| 3,702,027 A | 11/1972 | Marshall et al. | |
| 3,760,503 A | 9/1973 | Baskas | |
| 3,890,710 A | 6/1975 | Jaeger | |
| 3,905,106 A | 9/1975 | Costa et al. | |
| 3,932,939 A | 1/1976 | Weissman | |
| 3,937,773 A | 2/1976 | Huffman | |
| 4,122,606 A | 10/1978 | Roman | |
| 4,173,505 A * | 11/1979 | Jacobs | 156/285 |
| 4,265,619 A | 5/1981 | Lucki et al. | |
| 4,368,042 A | 1/1983 | Felstead et al. | |
| 4,374,076 A | 2/1983 | Stephan et al. | |
| 4,475,888 A * | 10/1984 | Gores et al. | 433/42 |
| 4,494,934 A | 1/1985 | Huffman | |
| 4,529,384 A | 7/1985 | Severy | |
| 4,657,992 A | 4/1987 | Brennan et al. | |
| 4,755,139 A | 7/1988 | Abbatte et al. | |
| 4,767,330 A | 8/1988 | Burger | |
| 4,798,534 A | 1/1989 | Breads | |
| 4,828,117 A | 5/1989 | Panzera et al. | |
| 4,856,991 A | 8/1989 | Breads et al. | |
| 4,936,862 A | 6/1990 | Walker et al. | |
| 4,943,237 A | 7/1990 | Bryan | |
| 5,011,405 A | 4/1991 | Lemchen | |

(Continued)

*Primary Examiner*—Ralph A Lewis

(57) ABSTRACT

A system for organizing dental aligners for a subject includes a plurality of dental aligners configured to move the subject's teeth at different steps of an orthodontic treatment and one or more connectors (including frangible connectors) configured to connect a plurality of dental aligners in an order that is consistent with the sequence in which the dental aligners are to be used by the subject in the orthodontic treatment.

20 Claims, 5 Drawing Sheets

U.S. PATENT DOCUMENTS

| | | | |
|---|---|---|---|
| 5,035,613 A | 7/1991 | Breads et al. | |
| 5,055,039 A | 10/1991 | Abbatte et al. | |
| 5,059,118 A | 10/1991 | Breads et al. | |
| 5,131,844 A | 7/1992 | Marinaccio et al. | |
| 5,183,479 A * | 2/1993 | Grimes | 51/293 |
| 5,186,623 A | 2/1993 | Breads et al. | |
| 5,273,429 A | 12/1993 | Rekow et al. | |
| 5,326,260 A * | 7/1994 | Klein et al. | 433/11 |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,452,219 A | 9/1995 | Dehoff et al. | |
| 5,466,152 A | 11/1995 | Walter | |
| RE35,263 E | 6/1996 | Silva et al. | |
| 5,549,476 A | 8/1996 | Stern | |
| 5,587,912 A | 12/1996 | Andersson et al. | |
| 5,607,305 A | 3/1997 | Andersson et al. | |
| 5,616,899 A | 4/1997 | Recigno | |
| 5,645,421 A | 7/1997 | Slootsky | |
| 5,762,192 A * | 6/1998 | Jacobs et al. | 206/369 |
| 5,788,489 A | 8/1998 | Huffman | |
| 5,879,158 A | 3/1999 | Doyle et al. | |
| 5,911,580 A | 6/1999 | Sharp et al. | |
| 5,927,984 A | 7/1999 | Lin | |
| 5,975,893 A | 11/1999 | Chishti et al. | |
| 6,217,325 B1 | 4/2001 | Chishti et al. | |
| 6,227,850 B1 | 5/2001 | Chishti et al. | |
| 6,227,851 B1 | 5/2001 | Chishti et al. | |
| 6,261,098 B1 | 7/2001 | Persson | |
| 6,299,440 B1 | 10/2001 | Phan et al. | |
| 6,309,215 B1 | 10/2001 | Phan et al. | |
| 6,423,252 B1 | 7/2002 | Chun et al. | |
| 6,425,759 B1 | 7/2002 | Cronin | |
| 6,497,574 B1 | 12/2002 | Miller | |
| 6,499,997 B2 | 12/2002 | Chishti et al. | |
| 6,524,101 B1 | 2/2003 | Phan et al. | |
| 6,541,074 B2 | 4/2003 | Cho | |
| 6,554,611 B2 | 4/2003 | Chishti et al. | |
| 6,572,372 B1 | 6/2003 | Phan et al. | |
| 6,582,227 B2 | 6/2003 | Phan et al. | |
| 6,582,229 B1 | 6/2003 | Miller et al. | |
| 6,602,070 B2 | 8/2003 | Miller et al. | |
| 6,607,382 B1 | 8/2003 | Kuo et al. | |
| 6,621,491 B1 | 9/2003 | Baumrind et al. | |
| 6,626,666 B2 | 9/2003 | Chishti et al. | |
| 6,626,669 B2 | 9/2003 | Zegarelli | |
| 6,629,840 B2 | 10/2003 | Chishti et al. | |
| 6,633,789 B1 | 10/2003 | Nikolskiy et al. | |
| 6,665,570 B2 | 12/2003 | Pavloskaia et al. | |
| 6,682,346 B2 | 1/2004 | Chishti et al. | |
| 6,685,469 B2 | 2/2004 | Chishti et al. | |
| 6,685,470 B2 | 2/2004 | Chishti et al. | |
| 6,688,886 B2 | 2/2004 | Hughes et al. | |
| 6,699,037 B2 | 3/2004 | Chishti et al. | |
| 6,705,861 B2 | 3/2004 | Chishti et al. | |
| 6,722,880 B2 | 4/2004 | Chishti et al. | |
| 6,726,478 B1 | 4/2004 | Isiderio et al. | |
| 6,729,876 B2 | 5/2004 | Chishti et al. | |
| 6,846,179 B2 | 1/2005 | Chapouland et al. | |
| 6,882,894 B2 | 4/2005 | Durbin et al. | |
| 6,913,462 B2 | 7/2005 | Honstein et al. | |
| 6,923,649 B2 | 8/2005 | Oswald et al. | |
| 6,981,874 B2 * | 1/2006 | Allred et al. | 433/215 |
| 7,040,897 B2 * | 5/2006 | Fischer et al. | 433/216 |
| 7,153,135 B1 | 12/2006 | Thomas | |
| 7,186,760 B2 | 3/2007 | Rudo | |
| 7,250,611 B2 | 7/2007 | Aguirre et al. | |
| 2001/0002310 A1 | 5/2001 | Chishti et al. | |
| 2001/0027401 A1 | 10/2001 | Klein | |
| 2001/0037248 A1 | 11/2001 | Klein | |
| 2002/0015934 A1 | 2/2002 | Rubbert et al. | |
| 2002/0017998 A1 | 2/2002 | Price | |
| 2002/0150855 A1 | 10/2002 | Chishti et al. | |
| 2002/0187451 A1 | 12/2002 | Phan et al. | |
| 2003/0002089 A1 | 1/2003 | Vadnais et al. | |
| 2003/0003416 A1 | 1/2003 | Chishti et al. | |
| 2003/0039940 A1 | 2/2003 | Miller | |
| 2003/0203334 A1 | 10/2003 | Hedge et al. | |
| 2003/0207227 A1 * | 11/2003 | Abolfathi | 433/24 |
| 2004/0063060 A1 | 4/2004 | Meyers et al. | |
| 2004/0109783 A1 | 6/2004 | Prasad et al. | |
| 2004/0115587 A1 | 6/2004 | Breining et al. | |
| 2004/0197728 A1 | 10/2004 | Abolfathi et al. | |
| 2004/0234929 A1 * | 11/2004 | Fischer et al. | 433/215 |
| 2005/0003319 A1 * | 1/2005 | Kuo | 433/6 |
| 2005/0186150 A1 * | 8/2005 | Allred et al. | 424/53 |
| 2005/0186526 A1 | 8/2005 | Stewart et al. | |
| 2006/0093982 A1 | 5/2006 | Wen | |
| 2006/0093987 A1 | 5/2006 | Wen | |
| 2006/0093992 A1 | 5/2006 | Wen | |
| 2006/0093993 A1 | 5/2006 | Wen | |
| 2006/0127838 A1 | 6/2006 | Liu et al. | |
| 2006/0127850 A1 | 6/2006 | Wen | |
| 2006/0127851 A1 | 6/2006 | Wen | |
| 2006/0134580 A1 | 6/2006 | Raby et al. | |
| 2006/0275736 A1 * | 12/2006 | Wen et al. | 433/213 |

* cited by examiner

SYSTEM FOR ORGANIZING DENTAL ALIGNERS

TECHNICAL FIELD

This application generally relates to the field of dental care, and more particularly to the field of orthodontics.

CROSS-REFERENCES TO RELATED INVENTIONS

The present invention is related to the following U.S. Provisional Patent Applications: U.S. Provisional Patent Application Ser. No. 60/675,003, filed Apr. 25, 2005, U.S. Provisional Patent Application Ser. No. 60/676,546, filed Apr. 29, 2005, U.S. Provisional Patent Application Ser. No. 60/676,278, filed Apr. 29, 2005, U.S. Provisional Patent Application Ser. No. 60/676,100, filed Apr. 29, 2005, and U.S. Provisional Patent Application Ser. No. 60/676,546, titled "Digitization of dental arch model components" by Huafeng Wen et al., filed Apr. 29, 2005. All of these provisional patent applications are herein incorporated by reference in their entirety.

The present invention is also related to the following U.S. Patent Applications: U.S. patent application Ser. No. 11/107,584, titled "Digital aligner devices having snap-on features" by Huafeng Wen et al, filed Apr. 15, 2005, U.S. patent application Ser. No. 11/074,301, titled "Dental aligner for providing accurate dental treatment" by Liu et al, filed Mar. 7, 2005, U.S. patent application Ser. No. 11/074,297, titled "Producing wrinkled dental aligner for dental treatment" by Liu et al, filed Mar. 7, 2005, U.S. patent application Ser. No. 11/074,300, titled "Fluid permeable dental aligner" by Huafeng Wen, filed Mar. 7, 2005, U.S. patent application Ser. No. 11/074,298, titled "Disposable dental aligner by Huafeng Wen, filed Mar. 7, 2005, U.S. patent application Ser. No. 11/050,051, titled "Storage system for dental devices" by Huafeng Wen, filed Feb. 3, 2005, U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, U.S. patent application Ser. No. 10/979,824, titled "Producing a base for physical dental arch model" by Huafeng Wen, filed Nov. 2, 2004, U.S. patent application Ser. No. 11/013,152, titled "A base for physical dental arch model" by Huafeng Wen, filed Dec. 14, 2004, U.S. patent application Ser. No. 11/012,924, titled "Accurately producing a base for physical dental arch model" by Huafeng Wen, filed Dec. 14, 2004, U.S. patent application Ser. No. 11/013,145, titled "Fabricating a base compatible with physical dental tooth models" by Huafeng Wen, filed Dec. 14, 2004, U.S. patent application Ser. No. 11/013,156, titled "Producing non-interfering tooth models on a base" by Huafeng Wen, filed Dec. 14, 2004, U.S. patent application Ser. No. 11/013,160, titled "System and methods for casting physical tooth model" by Huafeng Wen, filed Dec. 14, 2004, U.S. patent application Ser. No. 11/013,159, titled "Producing a base for accurately receiving dental tooth models" by Huafeng Wen, filed Dec. 14, 2004, and U.S. patent application Ser. No. 11/013,157, titled "Producing accurate base for dental arch model" by Huafeng Wen, filed Dec. 14, 2004. The disclosure of these related applications are herein incorporated herein by reference in their entirety.

BACKGROUND

Orthodontics is the practice of manipulating a subject's teeth to provide better function and appearance. In general, brackets are bonded to a subject's teeth and coupled together with an arched wire. The combination of the brackets and wire provides a force on the teeth causing them to move. Once the teeth have moved to a desired location and are held in place for a certain period of time, the body adapts bone and tissue to maintain the teeth in the desired location. A subject may be fitted with a retainer to help keep the teeth in the desired location.

Orthodontists initially base their treatment on a mental image of the subject's physical orthodontic structure and a mental image of a desired physical orthodontic structure for the subject, which may be assisted by x-rays and/or models. Based on these mental images, the orthodontist relies on his/her expertise to place the brackets and/or bands on the teeth and to manually bend (i.e., shape) wire, such that a force is asserted on the teeth to reposition them into the desired physical orthodontic structure. As the teeth move towards the desired location, the orthodontist makes continual judgments as to the progress of the treatment, the next step in the treatment (e.g., new bend in the wire, reposition or replace brackets, head gear, etc.), and the success of the previous step.

In general, an orthodontist makes manual adjustments to the wire and/or replaces or repositions brackets based on his or her expert opinion. Unfortunately, in the oral environment, it is difficult for a human being to accurately develop a visual three-dimensional image of an orthodontic structure due to the limitations of human sight and the physical structure of a human mouth. In addition, it is difficult (if not impossible) to accurately estimate three-dimensional wire bends (with accuracy within a few degrees) and to manually apply such bends to a wire. Further, it is difficult (or impossible) to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the success and speed of the process being dependent on the orthodontist's motor skills and diagnostic expertise. As a result of multiple wire changes, cost and subject discomfort is increased. The quality of care may also vary greatly from orthodontist to orthodontist, as does the time to treat a subject.

The practice of orthodontics relies heavily on the expert opinions and judgments of the orthodontist. Many innovations have been developed to aid orthodontists and other medical professionals attempting to align teeth. For example, U.S. Pat. No. 5,518,397 to Andreiko, et. al. provides a method of forming an orthodontic brace. The method includes obtaining a model of a subject's teeth and a prescription of desired positioning of the teeth. The contour of the subject's teeth is determined from the model. Calculations of the contour and the desired positioning of the subject's teeth are made and custom brackets are then created for receiving an arch wire to form an orthodontic brace system. The device of U.S. Pat. No. 5,518,397 places an arched wire on the bracket in a progressive curvature in a horizontal plane and a substantially linear configuration in a vertical plane. The brackets are customized to provide three-dimensional movement of the teeth. U.S. Pat. No. 5,518,397 to Andreiko, et. al., and all of the patents and references referred to in this specification, is hereafter incorporated by reference in their entirety.

Other innovations relating to bracket and bracket placements have also been patented. For example, such patent innovations are disclosed in U.S. Pat. No. 5,618,716 entitled "Orthodontic Bracket and Ligature" (a method of ligating arch wires to brackets), U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth."

Kuroda et al. (1996) Am. J. Orthodontics 110:365-369 describes a method for laser scanning a plaster dental cast to produce a digital image of the cast. See also U.S. Pat. Nos. 5,605,459, and 5,533,895; 5,474,448; 5,454,717; 5,447,432; 5,431,562; 5,395,238; 5,368,478; and 5,139,419, assigned to Orinco Corporation, describing methods for manipulating digital images of teeth for designing orthodontic appliances.

Realistic simulations of teeth position are extremely helpful to many orthodontic treatment processes. Orthodontists may use plaster models of the upper and lower arch, to create a set-up that may be manipulated to model the starting and finishing positions of teeth. Thus, the teeth may be modeled to help eliminate guesswork. Brackets may be bonded to each tooth model to show the orthodontist the geometry of the wire to run through the bracket slots to achieve a desired result. The bracket position may then be transferred to the original malocclusion model. To make sure that the brackets will be bonded at exactly this position at the real subject's teeth, small templates for every tooth can be fabricated that fit over the bracket and a relevant part of the tooth and allow for reliable placement of the bracket on the subject's teeth. Alternatively, a transfer tray may be fabricated for each arch by placing each single bracket onto a model of the malocclusion and then fabricating a single transfer tray per arch that covers all brackets and relevant portions of every tooth. Thus, a transfer tray may help assure a very quick and yet precise bonding using indirect bonding.

U.S. Pat. No. 5,431,562 to Andreiko et al. describes a computerized, appliance-driven approach to orthodontics in which shape information of teeth is acquired and a target arcform is calculated from the shape information. The shape of customized bracket slots, the bracket base, and the shape of the orthodontic archwire, are calculated in accordance with a mathematically-derived target archform. However, the orthodontist does not substantially interact with the appliance design.

Align Technology, Inc. also offers transparent, removable aligning devices. In this system, an orthodontist obtains an impression model of a subject's dentition and ships this model to a remote appliance manufacturing center, where it is scanned with a CT scanner. A computer model of the dentition in a final target situation is generated at the appliance manufacturing center and made available for viewing to the orthodontist over the Internet. The orthodontist indicates changes he or she wishes to make to individual tooth positions. A revised virtual model is provided for the orthodontist to review, until the target situation is agreed upon. A series of removable aligning devices (or shells) are manufactured and delivered to the orthodontist. The shells will move the subject's teeth to the desired or (final) target position.

U.S. Pat. No. 6,699,037 describes improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of successive steps. The individual appliances preferably comprise a polymeric shell having the teeth-receiving cavity formed therein, typically by molding. Each individual appliance is configured so that its tooth-receiving cavity has a geometry corresponding to an intermediate or end tooth arrangement intended for that appliance. That is, when an appliance is first worn by the subject, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step. U.S. Pat. Nos. 6,471,511 and 6,682,346 describe a stereo lithographic fabrication process.

Modeling a subject's teeth, such as modeling the upper or lower dental arches (including the manner in which the teeth interact) may be an important feature in using and creating an alignment device. A model of the subject's teeth can help guide the desired movement of the subject's teeth during an orthodontic treatment. The model can help avoid interference between a subject's teeth when undergoing dental re-alignment. A model can also provide input for the design and manufacturing of dental aligner devices.

Another challenge for orthodontic treatment using removable aligning devices is to accurately and effectively organize the sequence of aligners (e.g., both upper and/or lower aligners) used for the treatment. An entire sequence of aligners may be determined prior to beginning treatment. Thus, an entire series of aligners may be fabricated at once. It may be difficult to organize, present, or dispense the aligners so that a subject for whom the aligners are intended is able to select and wear them in the proper (e.g., the intended) order. Preparing an entire series of aligners at once may ultimately save in cost, treatment time, and may also enhance user comfort.

The systems and methods described herein may address some of the challenges identified above.

SUMMARY OF THE INVENTION

The present invention provides systems and methods to manufacture and organize aligners. Implementations of the system may include one or more of the following.

In one aspect, the present invention relates to a system for organizing dental aligners for a subject, including a plurality of dental aligners configured to move the subject's teeth at different steps of an orthodontic treatment, and one or more frangible connectors configured to connect the plurality of dental aligners so that the dental aligners can be disconnected from each other in the sequence that the dental aligners are to be used at the different steps of the orthodontic treatment. The frangible connectors may be made of substantially the same material as the aligners, or they may be a separate material. In general, the frangible connectors are manually breakable; thus the dental aligners may be separated from each other by the subject without requiring any additional tools. In some variations, the frangible connectors are breakable using a tool. A specific tool may be provided.

The aligners may include a shell portion having an outer surface, and an inner surface wherein the inner surface is configured to contact a subject's tooth, a bottom portion configured to be placed near the gingiva of the subject's tooth, and a tip portion on the side of the dental aligner opposite from the bottom portion. The shell portion may comprise a fluid-permeable material that allows fluid to communicate between a subject's tooth and at least a portion of the outer surface. The dental aligners linked by the connector(s) may have one or more wrinkled surfaces over at least a region of the shell portion, the bottom portion or the tip portion. Furthermore, the dental aligners may be made of any appropriate material, including one or more of: a polymeric material, a plastic, a urethane, an epoxy, a plaster, a stone, a clay, an acrylic, a metal, a wood, a paper, a ceramic, and a porcelain.

The manner in which the dental aligners are fabricated may determine the arrangement or nature of the connectors. For example, in some variations, the dental aligners are fabricated by vacuum forming using a plurality of dental arch models that correspond to configurations of the dental arch at different steps of the orthodontic treatment. The dental aligners may be fabricated by molding or CNC-based manufacturing. The dental aligners may be configured to connect to form a one-dimensional array or a two-dimensional array. These arrays may be organized in any appropriate way. For example, in some variations, the arrays of aligners are arranged so that the aligners are arranged "on top" of each other. For example, the upper region of one aligner (e.g., a tip portion) may be adjacent to the lower region (e.g., bottom portion) of another aligner. In some variations, the aligners are arranged side-by side.

The system may also include markings to indicate the sequence that the dental aligners are to be used by a subject. For example, the aligner may be marked, the connector may include markings, or an additional label may be included as part of the system. In some variations, the system may include a dispenser for dispensing the aligners in a predetermined sequence. For example, the dispenser may include interconnected chambers that hold individual (or pairs, such as upper and lower pairs of) aligners. In some variations, the dispenser is a container (e.g., a box, tube, etc.) that only permits the sequential release of a single aligner at a time (or the matching upper and lower aligners).

Also described herein are methods for organizing dental aligners for a subject. In some variations, the methods include the steps of determining a sequence that a subject will use the plurality of dental aligners in an orthodontic treatment (wherein the dental aligners are configured to move the subject's teeth in a plurality of steps during the orthodontic treatment) and fabricating a connected array of dental aligners (wherein the dental aligners are disposed in the connected array so that they may be removed from the connected array in the same sequence as the sequence to be used by the subject in the orthodontic treatment). The connected array comprises a one-dimensional array of the dental aligners or a two-dimensional array of the dental aligners.

The method may include the step of marking the connected array to indicate treatment order. The method may also include the step of fabricating the connected array of dental aligners using a plurality of dental arch models that correspond to configurations at different steps of the orthodontic treatment. In some variations, the method includes the step of vacuum forming the connected array of dental aligners to from a sheet of aligner-making material using a plurality of dental arch models that correspond to configurations at different steps of the orthodontic treatment.

In some variations, the step of fabricating the connected array of dental aligners comprises the steps of fabricating the dental aligners, and connecting the dental aligners in a connected array. The step of fabricating the connected array of dental aligners may include fabricating the dental aligners in a sheet of an aligner-making material, and cutting the sheet of the aligner-making material having the fabricated dental aligners to produce the connected array of dental aligners.

Additional methods for organizing dental aligners for a subject may include the steps of determining the sequence for a plurality of dental aligners to be used by the subject in an orthodontic treatment, wherein the dental aligners are configured to be applied in a plurality of steps in the orthodontic treatment to move the subject's teeth, and vacuum forming a connected array of dental aligners using a plurality of dental arch models that correspond to configurations of the dental aligners at different steps of the orthodontic treatment. In some variations, the step of vacuum forming the connected array of dental aligners comprises fabricating the dental aligners in a sheet of an aligner-making material using the plurality of dental arch models, and cutting the sheet of the aligner-making material having the fabricated dental aligners to produce a connected array of dental aligners. The dental aligners may be disposed in the array in the same sequence as the sequence that the plurality of dental aligners is to be used by the subject.

In some variations, the dental aligners are disposed in a one-dimensional array or a two-dimensional array.

Embodiments may include one or more of the following advantages. The disclosed system and methods may provide convenient ways for a subject to organize and track the dental aligners he or she uses in an orthodontic treatment process. Dental aligners for a subject's treatment can be connected by connectors and disposed in an array. In some variations, the connectors can be broken off manually by a subject, allowing easy disconnection between the adjacent dental aligners.

The dental aligners to be used at different treatment steps can be organized in the same order as the sequence of the treatment steps. This may decease the chance for errors when using the aligners. The systems and methods may be intuitive to use, and are typically inexpensive to produce. The systems and methods can also provide multiple dental aligners at one treatment step.

The array (or set) of the connected dental aligners provided may also be easily carried and stored. This can reduce or eliminate the need for a dedicated storage system for the dental aligners. Furthermore, these systems and methods may simplify or eliminate the need for labeling for the aligners.

The details of one or more variations of the invention are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention.

DESCRIPTION OF INVENTION

Figure 1:
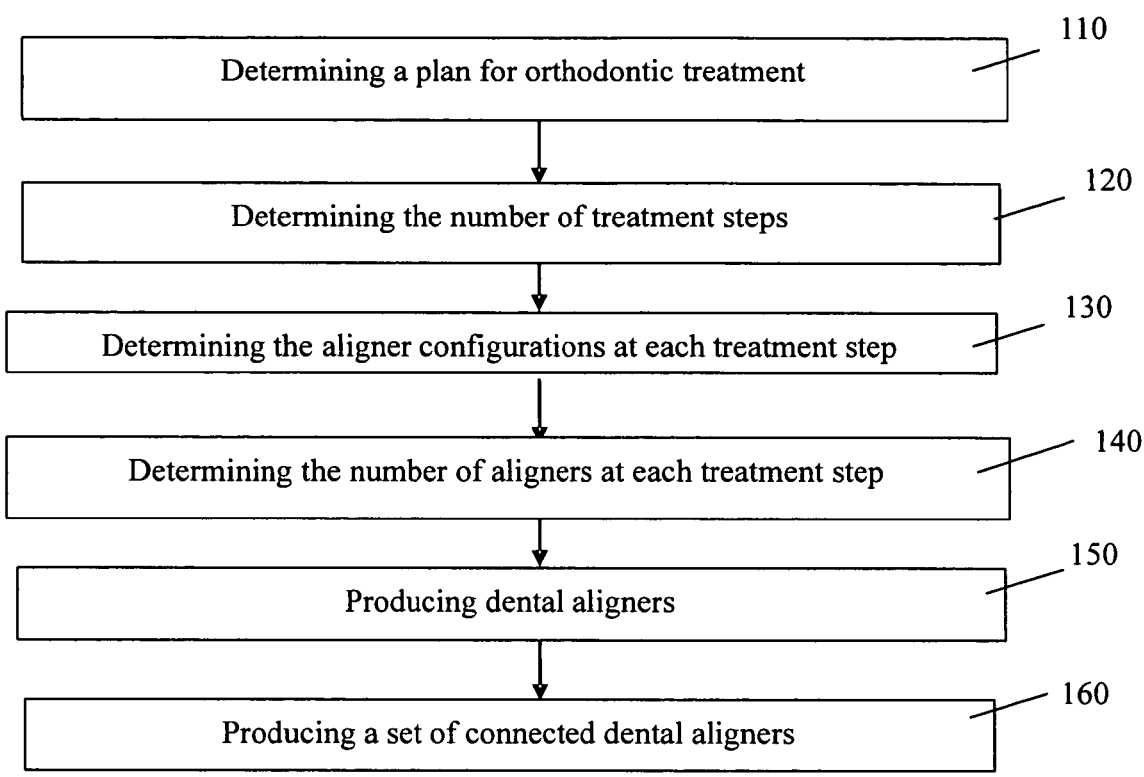
FIG. 1 is a flow chart showing one method of fabricating a set of connected dental aligners for a dental treatment as described herein.

The following detailed description should be read with reference to the drawings. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated, this invention need not be limited to applications in orthodontic treatments. As one of ordinary skill in the art having the benefit of this disclosure would appreciate, variations of the invention may be utilized in various other dental applications, such as fabrication of and/or treatment planning for dental crowns, dental bridges, and aligners. The dental models may also be modified to support research and/or teaching applications. Moreover, it should be understood that variations of the present invention may be applied in combination with various dental diagnostic and treatment devices to improve the condition of a subject's teeth.

It must also be noted that, as used in this specification and the appended claims, the singular forms "a," "an" and "the" include plural referents unless the context clearly dictates otherwise. Thus, for example, the term "a tooth" is intended to mean a single tooth or a combination of teeth, "an arch" is intended to mean one or more arches (e.g. both upper and lower dental arches). Furthermore, as used herein, "calculating," and "formulating" may include the process of utilizing manual and/or computer calculations, such as those used to create a numeric representation of an object (e.g. a digital model) or to measure differences in tooth position. For example, a digital representation may comprise a file saved on a computer, wherein the file includes numbers that represent a three-dimensional projection of a tooth arch. In another variation, a digital representation comprises a data set including parameters that can be utilized by a computer program to recreate a digital model of the desired object.

As used herein, the term "dental aligner" may refer to a dental device for rendering corrective teeth movement or for correcting malocclusion. One or more dental aligners can be worn on the subject's teeth so that a subject wearing the dental aligners will gradually have his or her teeth repositioned by the dental aligner "pushing" (or pulling) against the teeth, or gums (gingiva). As used herein, a "subject" may include any subject (human or animal) whose dental structure (e.g., teeth, gingiva, etc.) may be modeled by the devices, methods, and systems described herein, including orthodontic patients.

Connectors

One or more dental aligners may be connected by one or more connectors so that they are ordered or organized in a sequence reflecting the order that the dental aligners are to be used at different steps of an orthodontic treatment. In general, this means that two or more dental aligners corresponding to different sequential steps of an orthodontic treatment are fabricated before delivery or use by a subject, and connected so that the user or a practitioner (e.g., an orthodontist, dentist, dental technician, etc.) can separate the dental aligners sequentially in the order that the steps are to be followed.

The use of a series of two or more dental aligners to treat a subject's teeth is described more fully in the related applications, incorporated by reference above. A set of dental aligners is designed based on the current and predicted position of the subject's teeth, and the aligners may then be fabricated. In some variations, the entire sequence of aligners may be designed and fabricated for use by the subject. In some variations, only a few of the aligners in a treatment series are manufactured at a time. The total number of aligners produced at any time may be ordered and connected as described herein.

For example, FIG. 1 illustrates one method of fabricating and connecting a set of dental aligners for a dental treatment. First, a practitioner determines a treatment plan for a subject, as indicated in step 110. The treatment plan may specify the initial configurations of the subject's teeth, and the final configurations for the subject's teeth. The treatment plan may also specify the number of treatment steps 120 Any of these steps may be performed manually or with machine (e.g., computer) assistance. The configuration of each tooth is determined at each treatment step 130. One or a number of dental aligners can be specified for the subject to wear at each treatment step 140. The order of these aligners, as well as the shape of the aligners, may be determined during this process, and the dental aligners may be fabricated 150. As mentioned, two or more of the dental aligners may be produced simultaneously or sequentially. The fabrication of these aligners is described more fully below. The aligners may be fabricated so that they are connected, or they may be fabricated separately and then connected 160. Once connected, the aligners may be further packaged, or may be delivered as-is.

Any appropriate connector may be used to connect the plurality of dental aligners. For example, the connectors may be a physical link attached to each aligner (e.g., a frangible or detachable connector). In some variations, the connectors encompass at least a part of the aligners and thereby hold the aligners in the proper sequence or position. Two or more aligners linked by the connector(s) may be referred to as an array of aligners. As described more fully below, an array of aligners may comprise any number of aligners, arranged in any appropriate fashion (e.g., linearly, as a sheet, as a stack, etc.). Individual aligners may be removed from the array by removing the connector(s) linking the aligner to the array.

In some variations, the connectors are breakable connectors. For example, a connector may comprise a frangible connector. A frangible connector may be a manually breakable connector. A frangible connector may be made of a material that is brittle and can be broken by a person applying force using their hands. A frangible connector may comprise a polymer, ceramic, composite material, etc. In some variations, the frangible connector is serrated, scored, or may otherwise provide a fracture line or point that may guide or assist breaking the connector. For example, the frangible connector may have an hourglass (symmetrically tapered) shape, or any other appropriate shape providing a small cross-sectional area that is readily broken or separated.

The connectors may also be detachable connectors. For example, the connectors may comprise a fastener that can be unfastened. In some variations, the connectors may include snaps, buttons, clasps, links, etc. Thus, the connectors may be single-use or reusable. The connectors may be attached directly to two or more aligners, or they may be indirectly attached. The connector may be a single piece, or it may be two or more pieces. For example, the connector may have two pieces that mate to connect two or more aligners. Thus, one part of the connector may be linked to one aligner, and another part of the connector may be linked to another aligner. The two aligners are connected when the parts of the connector are joined (e.g., mated, interlocked, or fastened).

A connector may be part of a larger frame. For example, a series of aligners may be linked to connectors that form a single frame. Thus, the aligners are connected to each other through a frame or framework. The connectors link the aligner to the frame. The frame may be a separate structure from the connectors, or the connectors may be parts of the frame. The frame may keep the aligners organized, and may also provide additional support or structure that may help store the aligners.

Aligners may be linked to other aligners by a single connector or by multiple connectors. For example, different connectors may link to different portions of an aligner. Two aligners may also be linked by more than one connector (including more than one type of connector).

As mentioned above, a connector may be directly attached to one or more aligners. For example, the connectors may be formed from the same material as the aligner. The connector may be fabricated at the time that the aligners are fabricated. For example, the connector may be a peg (e.g., a projection) or small piece of material that is left connecting two or more aligners after they have been fabricated. In some variations, the aligners are not fabricated together, but are connected after fabrication and linked to each other by being directly connected to one or more connectors.

In variations where the aligners are directly connected to the connectors, the connectors and aligners may be attached in any appropriate manner. For example, the connectors may be attached via an adhesive (e.g., glue, epoxy, etc). Thus, the connector may include different materials that are connected to the aligner. In some variations, the connectors themselves comprise an adhesive that may be set into position and hardened. In one variation, the connector comprises a dissolvable material (e.g., a starch, etc.) so that the connector may be severed by exposing the connectors to a solvent (e.g., water, alcohol, etc.).

Connectors may connect to any appropriate region of a dental aligner. In general, it may be desirable for the connector to link to the outer surface of the dental aligner shell. For example, a connector may attach to a region of the dental aligner that does not interact with portions of the subject's mouth, or with other dental aligners, when the subject is wearing the dental aligner. In some variations, the dental aligners are linked to connectors on the side of the outer region of the shell (e.g., between the tip region and the bottom region). In some variations, the connector connects to the inner portion of an aligner.

A connector may also be indirectly linked to an aligner and to other connectors. For example, an indirectly attached connector may secure the aligner (keeping the aligners in a predetermined sequence or position) by passing through a hole on the aligner, or may enclose a portion of the aligner. In some variations, the connector surrounds part of the aligner (or the entire aligner). For example, the connectors may be a set of joined chambers. In some variations, a connector comprises a series of chambers into which aligners fit. Each chamber may be closed off (e.g., by a removable cover) to hold the aligner therein. Thus, to remove the aligner, the chamber is opened, releasing the aligner.

The connectors may be separated manually or with the assistance of a tool or tools. For example, the connector may be manually severable by snapping, breaking, shattering, tearing, ripping, twisting, pulling, or the like, to apply enough force to remove the aligner. In some variations, the aligners themselves interlock, and the connector is a region of the aligner.

The connector may also be separated by a tool. For example, the connectors may be cut or broken by a blade, or devices having a blade (e.g., scissors, clippers, snips, etc). In some variations, the tools are specially adapted to remove the connector without damaging the aligner. For example, the tool my include a lip or sheath to protect the aligner as the tool cuts the connector.

The aligners are typically arranged in an array. As described above, an array may be any appropriate arrangement of aligners including one-dimensional (e.g., linear) arrangements, two dimensional arrangements (e.g., a sheet of aligners), and three-dimensional arrangements. The aligners may be ordered within the array so that a subject or practitioner can remove an aligner from the array in the order in which the aligner is to be provided for use, consistent with the treatment of the subject. For example, the aligners may be ordered sequentially so that the aligner at one end of the array is the first aligner (e.g., for the first week). As treatment progresses, the next aligner to be used is available at the end of the array, so that it can be easily identified and removed from the array for use. Thus, the array of connected aligners may be arranged so that the aligners are dispensed one (or two, e.g., when there are separate upper and lower aligners) at a time. Aligners corresponding to later periods of treatment may be accessed only after removing the aligners intended for earlier in the treatment.

EXAMPLES

Figure 2:
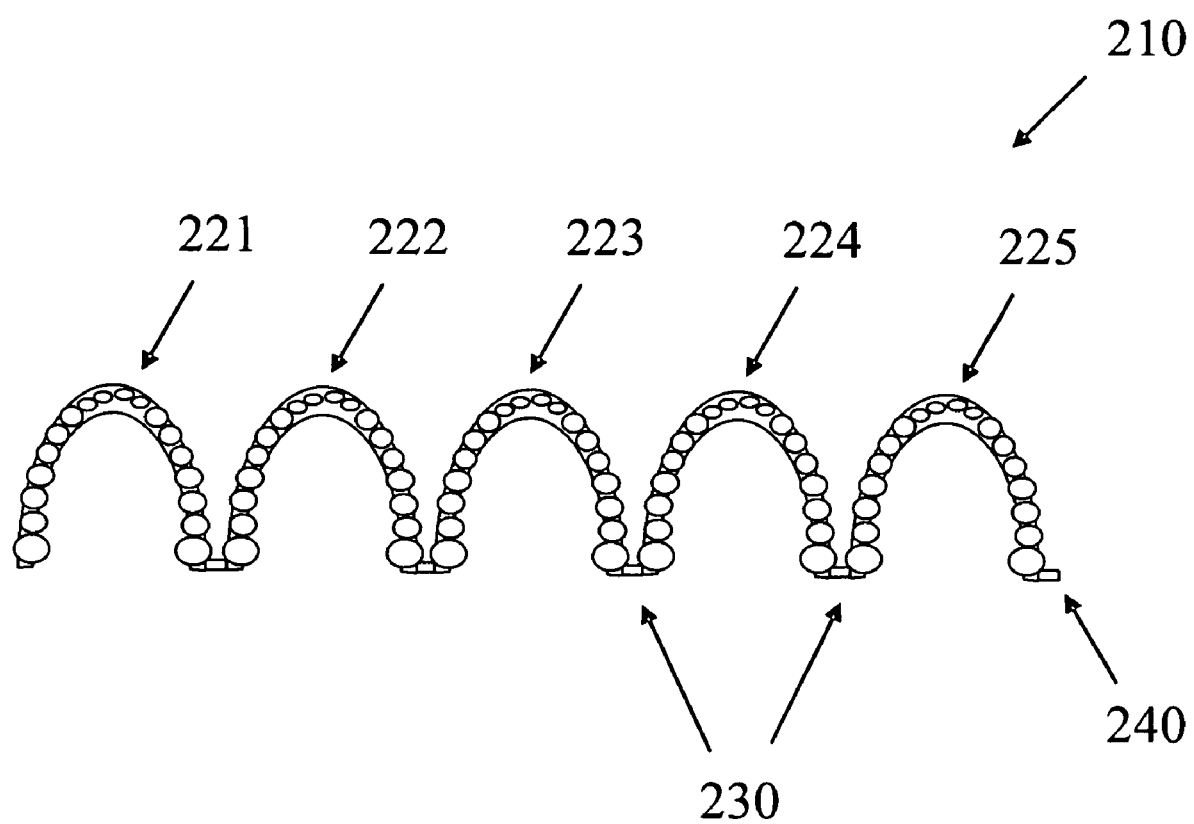
FIG. 2 is a top view of a one variation of a linear array of one connected dental aligners.

FIG. 2 shows one variation of an array of dental aligners. A linear array of adjacently connected dental aligners 210 includes a plurality of dental aligners 221-225 that are connected by a plurality of connectors 230. The aligners 221-225 are arranged in the same order as the treatment sequence to be used by the subject. For example, the first dental aligner in the linear series 221 is for the first treatment step; the second dental aligner 222 is intended for the second treatment step, and so on. The subject can break off each of the aligners 221-225 one at a time during the treatment. Thus, the aligners are arranged in the same order as the intended usage, which prevents the dental aligners 221-225 from being used out of the treatment sequence. The array of connected dental aligners may be easy to carry and store. This may also eliminate the need for a dedicated storage system for the dental aligners. Labeling the aligners can also be simplified or eliminated. For example, a label indicating the first aligner may be part of the connector 230, or may be attached to the connector. In one variation, the last aligner in the organized array 225 is connected to a label indicating that this is the last (and not the first) aligner.

Figure 3:
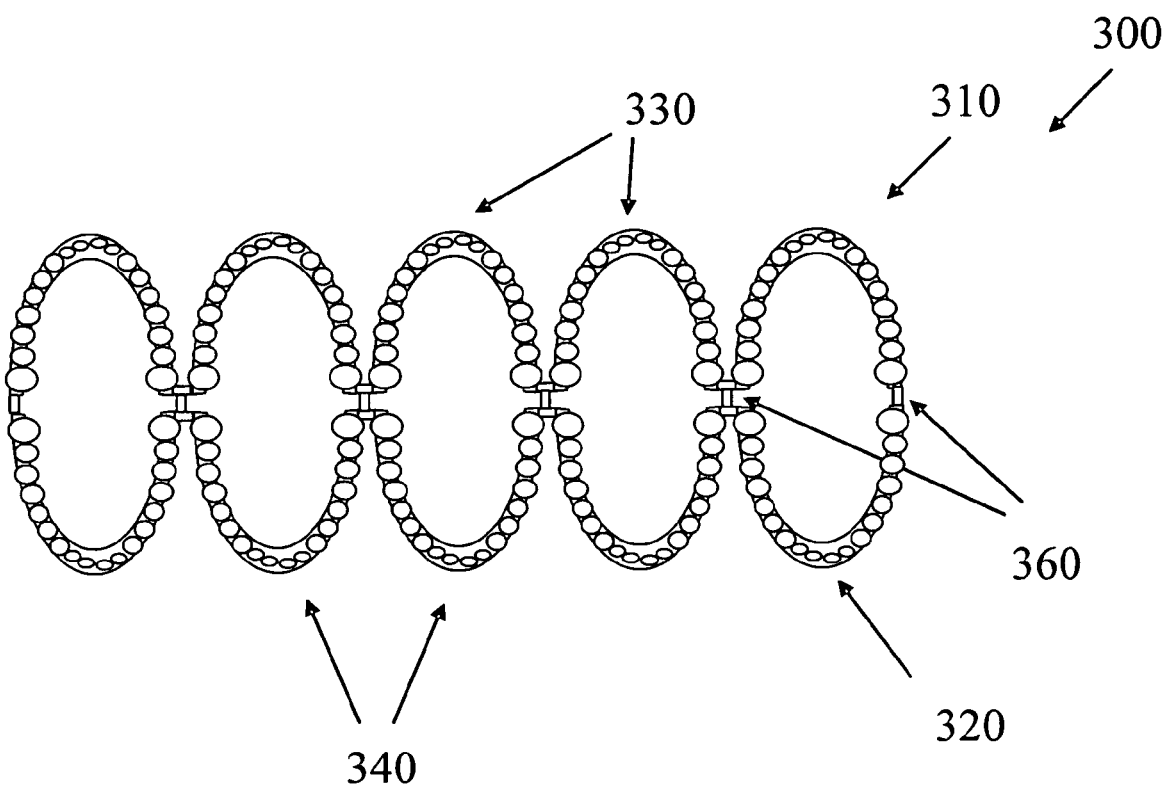
FIG. 3 is a top view of one variation of a two-dimensional array of connected dental aligners.

Another variation of a connected array of aligners is shown in FIG. 3. As in FIG. 1, the connectors are peg-like connectors that are directly connected to the aligners that they link. FIG. 3 shows a top view of a two-dimensional array 300 of connected dental aligners 330 and 340. In this example, the dental aligners 330 and 340 are disposed in two linear arrays 310 and 320, similar to the linear array shown in FIG. 1. Adjacent dental aligners 330 and 340 within or between the linear arrays 310 and 320 are connected by connectors 360. Thus, at least some of the connectors include links to four different aligners. The layout of a two-dimensional array structure can further help the subject to organize dental aligners. For example, in the example illustrated in FIG. 4, a column can correspond to identical or similar dental aligners to be used at a specific treatment step. The subject can break off aligners in a particular column at a treatment step. In one variation, the column may correspond to an upper arch and lower arch aligner of the same treatment step. In some variations, the column may comprise duplicate or alternative aligners for the same treatment step. After the subject moves to the next treatment step, he or she can use the next column of aligners.

Figure 4:
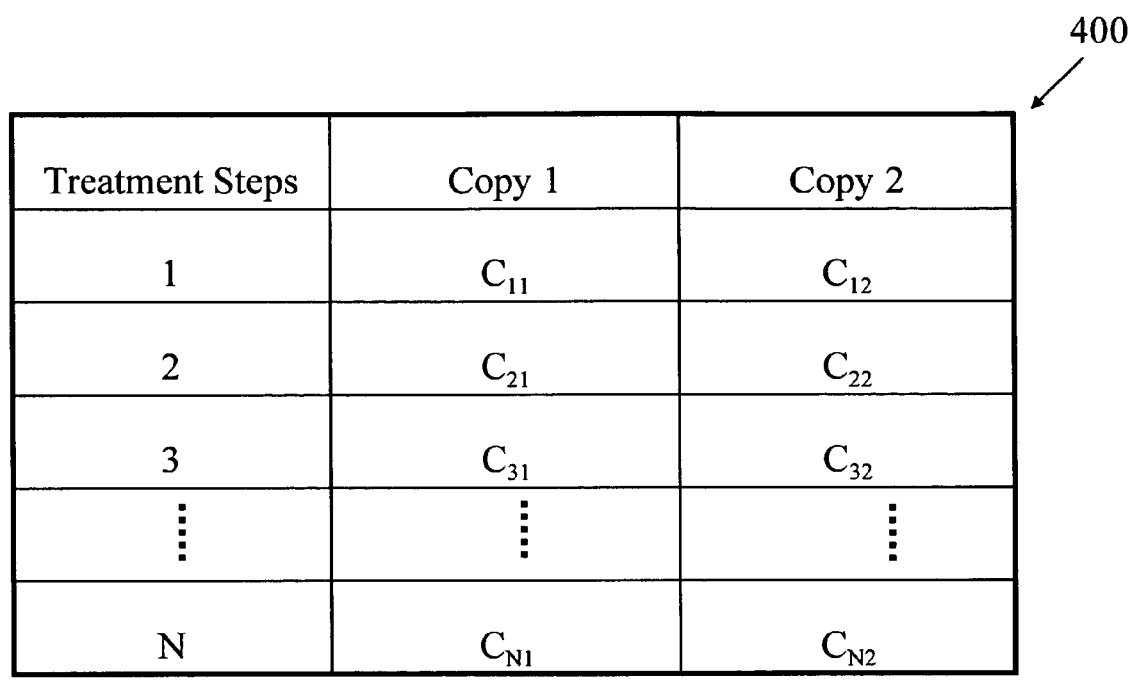
FIG. 4 shows a table listing dental aligners for a subject's orthodontic treatment.

FIG. 4 shows a table 400 that summarizes the dental aligners to be used for a subject's orthodontic treatment. The treatment can include a plurality of N steps. Each treatment step may include one or more copies of dental aligners. For example, $C_{11}$ and $C_{12}$ may correspond to dental aligners for the first step, $C_{21}$ and $C_{22}$ may correspond to dental aligners for the second step, and so on. A marking, label, or other indicator (such as "$C_{11}$" and "$C_{12}$") can be made on each of the dental aligners to further assist the tracking of the dental aligners for the subject, or the markings may occur on the connectors, or on a separate label connected to the aligner (e.g., via a connector) or to the connector. For example, in variations where the aligners are connected to a frame, the frame may include labels or markings. In general, the dental aligners used at each step can only be used for a short period of time and then are disposed. Details of disposable dental aligners are disclosed in the above referenced and U.S. patent application Ser. No. 11/074,298, titled "Disposable dental aligner by Huafeng Wen, filed Mar. 7, 2005, the disclosures of which are incorporated herein by reference.

The connectors shown in FIGS. 2 and 3 are all frangible tab-type connectors that may be manually disconnected by breaking the connection between the connector and the aligner. The connector may be broken off so that the surface of the aligner is left smooth where it was attached to the connector. This may prevent the aligner from having a sharp or irritating edge which may decrease the comfort of a subject wearing the aligner. In some variations, the connector has a relatively large structural strength compared to the interface between the connector and the aligner. For example, in FIG. 2, the connectors 230 have a central region that is larger than the tapered ends, where the connector links to the aligner. In some variations, the tapered ends of the connectors may also be configured to break in a known (e.g., stereotypical) pattern, such as a pattern that leaves the surface of the aligner relatively smooth. For example, the tapered ends may be creased, serrated, dimpled, perforated, etc.

The aligner at the far end of the array of aligners shown in FIG. 2 has a (partial) connector that is not shown linked to a second aligner 240. As mentioned above, connectors, including partial connectors, may be removed before wearing the aligner. In some variations, the connector may be left behind on the aligner, and the aligner may be used without removing the remaining portion of the connector.

Fabrication of Dental Aligners

Dental aligners as described herein can be fabricated in any appropriate fashion. For example, a number of processes disclosed in the above-referenced U.S. patent applications may be used to fabricate dental aligners, including dental aligners that are fabricated connected to each other as described.

In one variation, the dental aligners are formed by a vacuum-forming process. The subject's dental arch model is placed on a base plate of a vacuum former machine. A digital dental aligner model specifies a shell portion including an outer surface and an inner surface to be in contact with the subject's tooth, a bottom portion to be placed near the gingiva of the subject's tooth, and a tip portion on the opposite side of the bottom portion. The digital dental aligner model may also define one or more wrinkles formed over at least one of the outer surface of the shell portion, the inner surface of the shell portion, and the bottom portion. An apparatus produces a physical dental aligner having a wrinkled surface in accordance with the digital dental aligner model.

Figure 5:
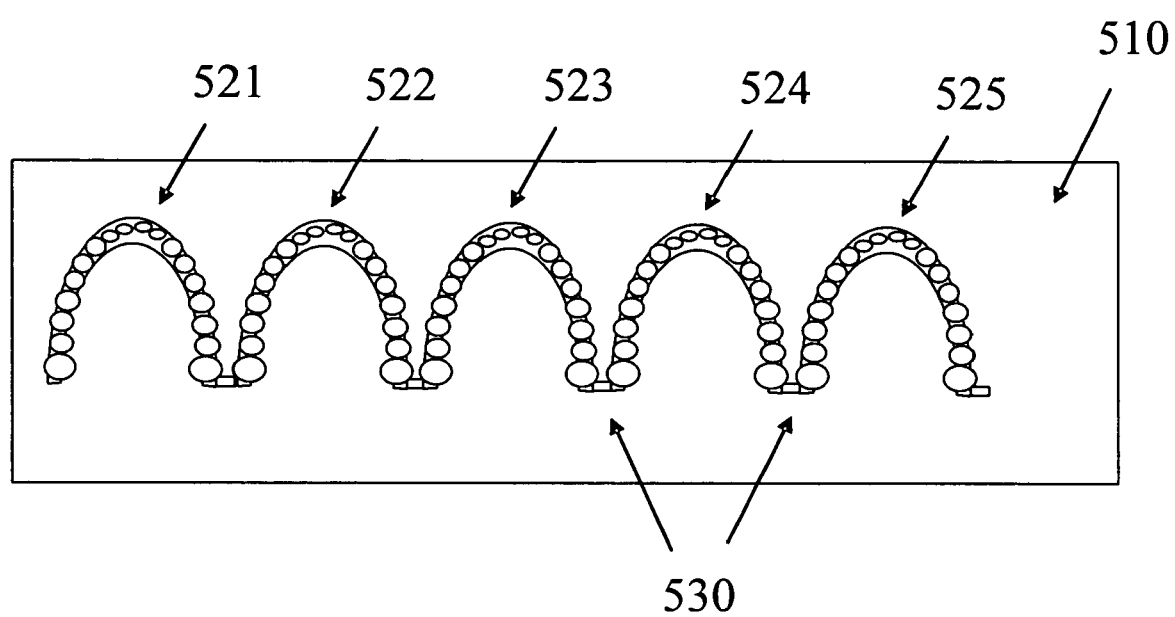
FIG. 5 illustrates one example of an arrangement for fabricating an array of connected dental aligner for a subject's orthodontic treatment.

FIG. 5 shows and example of a sheet 510 of aligner-making material attached to a sheet holder. This sheet is lifted up near a heating element in order to form the aligners. The sheet can be made of a uniform distribution of single material or comprise multiple layers of different materials. After the aligner-making material is heated for a specified time, the sheet holder is pressed on the subject's dental arch model on the base plate. A vacuum pump removes air at the bottom of the base plate to cause the softened aligner making material to relax and fittingly form around the surface the subject's dental arch model to produce a dental aligner 521 on the sheet 510.

A plurality of dental arch models can then be provided corresponding to the configurations of different treatment steps for the subject. The vacuum-forming process described above may be repeated using the dental arch models to produce aligners 522-525 on the sheet 510 of the aligner making material. The aligners 522-525 may be used by the subject at different treatment steps. The sheet 510 of the aligner making material is then cut out by a mechanical cutter, a laser cutter, a puncher or a die cut along the gingival lines of each of the aligners 521-525. The cuts leave a plurality of connectors 530 to keep the aligners 521-525 connected in an array.

Details of making dental arch models for a dental treatment are disclosed in the above-referenced and U.S. patent application Ser. No. 10/979,504, titled "Producing an adjustable physical dental arch model" by Huafeng Wen, filed Nov. 2, 2004, U.S. patent application Ser. No. 10/979,824, titled "Producing a base for physical dental arch model" by Huafeng Wen, filed Nov. 2, 2004, U.S. patent application Ser. No. 11/013,152, titled "A base for physical dental arch model" by Huafeng Wen, filed Dec. 14, 2004, U.S. patent application Ser. No. 11/012,924, titled "Accurately producing a base for physical dental arch model" by Huafeng Wen, filed Dec. 14, 2004, U.S. patent application Ser. No. 11/013,145, titled "Fabricating a base compatible with physical dental tooth models" by Huafeng Wen, filed Dec. 14, 2004, U.S. patent application Ser. No. 11/013,156, titled "Producing non-interfering tooth models on a base" by Huafeng Wen, filed Dec. 14, 2004, U.S. patent application Ser. No. 11/013,160, titled "System and methods for casting physical tooth model" by Huafeng Wen, filed Dec. 14, 2004, U.S. patent application Ser. No. 11/013,159, titled "Producing a base for accurately receiving dental tooth models" by Huafeng Wen, filed Dec. 14, 2004, and U.S. patent application Ser. No. 11/013,157, titled "Producing accurate base for dental arch model" by Huafeng Wen, filed Dec. 14, 2004, the disclosures of which are incorporated herein by reference in their entirety.

In some variations, dental aligners are fabricated using Computer Numerical Control (CNC) based manufacturing such as milling, stereo lithography, and laser machining. A digital arch model is first obtained by scanning a subject's dental impression. A digital aligner model is then developed based on the digital arch model. The digital aligner model can provide input data to the CNC based manufacturing. Aligner components can be fabricated by CNC manufacturing techniques. The aligner components can include features for attaching aligners to each other, including the connectors. The aligner components can be automatically assembled by robotic arms under computer control. The dental aligners may therefore be obtained by assembling the aligner components. Connectors (e.g., frangible connectors) can also be fabricated as part of the aligner components or separately, and may also be robotically assembled, or manually assembled. The connectors may be attached to the aligner components and connect adjacent aligners in the set.

Dental aligners can also be fabricated by molding. Malleable casting material can be poured into a casting container containing the subject's arch model. The container may then be sealed. Heating, pressure or UV light may be applied to cast the material so that it is solidified. A dental aligner may be formed, and can be detached from the container. Breakable connectors can also be fabricated. The breakable connectors can then be latched or locked to the adjacent aligners in a set of dental aligners for a treatment.

The dental aligners described herein can be made of a fluid permeable material to allow oxygen and/or a subject's saliva to pass through, which may improve oral hygiene and comfort. The dental aligners can include wrinkled surfaces to eliminate or reduce relaxation problem commonly seen in removable dental aligners. The dental aligner can also comprise surface textures that simulate the cosmetic appearance of teeth or that aid with attachment. Disposable dental aligners can be used for a short period of time. A plurality of disposable aligners can be provided for a subject at a treatment step. The dental aligner (and/or the connector) can be made of plastics, polymers, urethane, epoxy, plaster, stone, clay, acrylic, metals, wood, paper, ceramics, and porcelain. The dental aligner (and/or the connector) may comprise multiple layers, each comprising the same or different materials.

Details of making dental aligners using different techniques are disclosed in the above-referenced patent applications, including U.S. patent application Ser. No. 10/979,497, titled "Method and apparatus for manufacturing and constructing a dental aligner" by Huafeng Wen, filed Nov. 2, 2004, U.S. patent application Ser. No. 11/074,301, titled "Dental aligner for providing accurate dental treatment" by Liu et al., filed Mar. 7, 2005, U.S. patent application Ser. No. 11/074,297, titled "Producing wrinkled dental aligner for dental treatment" by Liu et al, filed Mar. 7, 2005, and U.S. patent application Ser. No. 11/074,300, titled "Fluid permeable dental aligner" by Huafeng Wen, filed Mar. 7, 2005, the disclosures of which are incorporated herein by reference in their entirety.

Use of Connectors and Connected Dental Aligners

As described above, the aligners may be sequentially arranged, so that they may be accessed and used in the proper order. In operation, the subject receiving and array of aligners may remove the aligner from the array in order to place the aligner against his or her teeth for treatment to straighten or otherwise manipulate the teeth. Removing the aligners releases the aligner from the array, and may require breaking the connector (e.g., frangible connectors), cutting the connector or removing the connecter from around or through the aligner, as described above.

Once the aligner has been removed, it may be used by the subject immediately, or it may undergo further processing. For example, the aligner may be smoothed, coated, rinsed, etc., in order to prepare the aligner for use.

The aligners (e.g., an array of aligners) may be part of a dental treatment system that includes additional components. For example, a dental treatment system may include a dispenser for dispensing the aligners in the order in which they should be used. A dispenser may comprise packaging. For example, the dispenser may be a tube or box in which a column of aligners is kept in the desired treatment order. The dispenser may have an opening through which each aligner may be removed, in the order that it is to be used by the subject. For example, the dispenser may be a tube for holding aligners in the desired order. In some variations, the connector comprises a dispenser.

A dental treatment system may also include instructions for using the aligner. The instructions may also include instructions for removing the aligner from an array of aligners, and/or for preparing the aligner for use. The instructions may also include instructions for inserting and wearing the aligner. These instructions may be in any appropriate form, including written, electronic, recorded (e.g., video, audio, etc.). In some variations, the instructions may be pictographic. The instructions may be written in any appropriate language.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention.

What is claimed is:

1. A method for organizing dental aligners for a subject, comprising:
    fabricating a plurality of dental aligners in a sheet of an aligner-making material using a plurality of dental arch models, wherein the plurality of aligners comprises at least one aligner having an alternative shape, wherein the dental aligners are configured to move the subject's teeth in a plurality of steps during the orthodontic treatment and wherein the plurality of aligners are in a sequential order representing an order in which the plurality of aligners will be worn by the subject; and
    cutting the sheet of the aligner-making material having the fabricated dental aligners along gingival lines of each of the aligners and removing sheet material cut from along the gingival lines, while maintaining a portion of the aligner-making material as a frangible connector between adjacent dental aligners, to form a connected array of dental aligners.

2. The method of claim 1, wherein the step of fabricating comprises:
    vacuum forming the plurality of dental aligners using a plurality of dental arch models that correspond to configurations of the dental aligners at different steps of an orthodontic treatment.

3. The method of claim 1, further comprising:
    determining a sequence for the plurality of dental aligners to be used by the subject in an orthodontic treatment, wherein the dental aligners are configured to be applied in a plurality of steps in the orthodontic treatment to move the subject's teeth.

4. The method of claim 3, wherein the dental aligners are disposed in the array in the sequence that the dental aligners are to be used by the subject.

5. The method of claim 1, wherein the dental aligners are disposed in a one-dimensional array or a two-dimensional array.

6. The method of claim 1, wherein the dental aligners are disposed in a two-dimensional array with a first dimension representing a sequence of treatment steps and a second dimension representing a plurality of duplicate dental aligners for a given treatment step.

7. The method of claim 1, wherein the dental aligners are disposed in a two-dimensional array with a first dimension representing a sequence of treatment steps and a second dimension representing an upper arch dental aligner and a lower arch dental aligner for a given treatment step.

8. A method for organizing dental aligners for a subject, comprising:
    determining a sequence that a plurality of dental aligners will be used by the subject in an orthodontic treatment, wherein the plurality of aligners comprises at least one aligner having an alternative shape, and wherein the dental aligners are configured to move the subject's teeth in a plurality of steps during the orthodontic treatment and wherein the plurality of aligners is in a sequential order representing an order in which the plurality of aligners will be worn by the subject; and fabricating a connected array of dental aligners, wherein the connected array comprises a first dimension representing a sequence of treatment steps and a second dimension comprising multiple aligners for use during a given treatment step and wherein the connected array of dental aligners is connected using a frangible portion aligner-making material wherein the second dimension of the connected array comprises an upper arch dental aligner and a lower arch dental aligner for the given treatment step.

9. The method of claim 8, wherein the second dimension of the connected array comprises a plurality of duplicate dental aligners for the given treatment step.

10. The method of claim 8, wherein fabricating the connected array of dental aligners comprises:

fabricating the plurality of dental aligners separately; and
connecting the plurality of dental aligners to form the connected array.

11. The method of claim 10, wherein fabricating the connected array of dental aligners further comprises:

fabricating a plurality of connectors; and
attaching the plurality of connectors to the plurality of dental aligners.

12. The method of claim 8, wherein fabricating the connected array of dental aligners comprises:

fabricating the plurality of dental aligners in a common sheet of aligner-making material; and
cutting the sheet of the aligner-making material, while maintaining a portion of the aligner-making material as a frangible connector between adjacent dental aligners, to form the connected array of dental aligners.

13. The method of claim 8, further comprising marking the connected array to indicate treatment order.

14. The method of claim 8, further comprising:

forming dissolvable connectors between adjacent dental aligners.

15. The method of claim 8, further comprising:

fabricating the plurality of dental aligners using a plurality of dental arch models that correspond to teeth configurations at different steps of the orthodontic treatment.

16. The method of claim 15, wherein fabricating the plurality of dental aligners comprises vacuum forming aligner material over the plurality of dental arch models.

17. The method of claim 8, wherein the plurality of dental aligners are fabricated with a CNC machine.

18. The method of claim 8, wherein the plurality of dental aligners are fabricated using a mold.

19. The method of claim 8, further comprising:

forming physical features on the plurality of dental aligners to receive a connector.

20. The method of claim 8, further comprising:

forming physical features on the plurality of dental aligners by which one dental aligner may be connected to one or more other dental aligners.

* * * * *